(12) United States Patent
Orbay (10) Patent No.: US 7,780,664 B2
(45) Date of Patent: Aug. 24, 2010

(54) ENDOSTEAL NAIL (75) Inventor: Jorge L. Orbay, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 520 days.

(21) Appl. No.: 10/985,594

(22) Filed: Nov. 10, 2004

(65) Prior Publication Data

US 2005/0065520 A1   Mar. 24, 2005

(51) Int. Cl.
*A61B 17/58* (2006.01)
(52) U.S. Cl. .................................................. 606/62
(58) Field of Classification Search .......... 606/62, 606/63, 64–67, 96–98, 87
See application file for complete search history.

(56) References Cited

U.S. PATENT DOCUMENTS

| | | | |
|---|---|---|---|
| 388,000 A | 8/1888 | Rider | |
| 472,913 A | 4/1892 | Taylor | |
| 1,151,861 A | 8/1915 | Brumback | |
| 2,056,688 A | 10/1936 | Peterka et al. | |
| 2,500,370 A | 3/1950 | McKibbin | |
| 2,526,959 A | 10/1950 | Lorenzo | |
| 2,614,559 A * | 10/1952 | Livingston | 606/64 |
| 2,821,979 A | 2/1958 | Cameron | |
| 3,025,853 A | 3/1962 | Mason | |
| 3,236,141 A | 2/1966 | Smith | |
| 3,645,161 A | 2/1972 | Wesker | |
| 3,709,218 A | 1/1973 | Halloran | |
| 3,717,146 A * | 2/1973 | Halloran | 606/64 |
| 3,741,205 A | 6/1973 | Markolf et al. | |

(Continued)

FOREIGN PATENT DOCUMENTS

CA    2174293 A    10/1997

(Continued)

OTHER PUBLICATIONS

"Advances in distal Radius Fracture Management (D)", transcript of American Academy of Orthopaedic Surgeons 2001 Conf.; pp. 134-151, Feb. 28, 2001 including Article by Matthew D. Putnam MD, "Repair and Rehabilitation of Distal Fractures: The Role of Subchondral Fixation" at pp. 144-147.

(Continued)

*Primary Examiner*—Thomas C Barrett
*Assistant Examiner*—Michael J Araj
(74) *Attorney, Agent, or Firm*—Gordon & Jacobson, PC (57) ABSTRACT

The system includes an elongate intramedullary nail which is rigidly fixed under compression to the endosteal surface of a bone with unicortical locking machine screws inserted through the bone and into a plurality of longitudinally displaced threaded holes in the nail. A jig is provided for drilling holes through the bone in alignment with the screw holes in the nail. The nail and jig each include anti-rotation structure at which the nail and jig can be coupled together in a fixed alignment. A method is also provided for implanting an intramedullary nail on two sides of a bone fracture, and clamping the bone with sufficient force to immobilize the fracture by forcing the implant against an endosteal surface of the bone and applying a compressive force against the outer surface of the bone.

19 Claims, 5 Drawing Sheets

U.S. PATENT DOCUMENTS

| | | | |
|---|---|---|---|
| 3,842,825 | A | 10/1974 | Wagner |
| 3,939,498 | A | 2/1976 | Lee et al. |
| RE28,841 | E | 6/1976 | Allgower et al. |
| 4,011,863 | A | 3/1977 | Zickel |
| 4,119,092 | A | 10/1978 | Gil |
| 4,135,507 | A | 1/1979 | Harris |
| 4,153,953 | A | 5/1979 | Grobbelaar |
| 4,169,470 | A | 10/1979 | Ender et al. |
| 4,172,452 | A | 10/1979 | Forte et al. |
| 4,408,601 | A | 10/1983 | Wenk |
| 4,467,793 | A | 8/1984 | Ender |
| 4,473,069 | A | 9/1984 | Kolmert |
| 4,483,335 | A | 11/1984 | Tornier |
| 4,484,570 | A | 11/1984 | Sutter et al. |
| 4,488,543 | A | 12/1984 | Tornier |
| 4,493,317 | A | 1/1985 | Klaue |
| 4,503,847 | A | 3/1985 | Mouradian |
| 4,506,662 | A | 3/1985 | Anapliotis |
| 4,565,193 | A | 1/1986 | Streli |
| 4,622,959 | A | 11/1986 | Marcus |
| 4,651,724 | A | 3/1987 | Berentey et al. |
| 4,712,541 | A | 12/1987 | Harder et al. |
| 4,733,654 | A | 3/1988 | Marino |
| 4,776,330 | A | 10/1988 | Chapman et al. |
| 4,790,302 | A | 12/1988 | Colwill et al. |
| 4,794,919 | A | 1/1989 | Nilsson |
| 4,800,874 | A | 1/1989 | David et al. |
| 4,867,144 | A | 9/1989 | Karas et al. |
| 4,915,092 | A | 4/1990 | Firica et al. |
| 4,923,471 | A | 5/1990 | Morgan |
| 4,955,886 | A | 9/1990 | Pawluk |
| 5,006,120 | A | 4/1991 | Carter |
| 5,013,313 | A | 5/1991 | Surer |
| 5,013,314 | A | 5/1991 | Firica et al. |
| 5,015,248 | A | 5/1991 | Burstein et al. |
| 5,035,697 | A | 7/1991 | Frigg |
| 5,041,113 | A | 8/1991 | Biedermann et al. |
| 5,057,110 | A * | 10/1991 | Kranz et al. .................. 606/62 |
| 5,085,660 | A | 2/1992 | Lin |
| 5,127,912 | A | 7/1992 | Ray et al. |
| 5,147,361 | A | 9/1992 | Ojima et al. |
| 5,151,103 | A | 9/1992 | Tepic et al. |
| 5,190,544 | A | 3/1993 | Chapman et al. |
| 5,197,966 | A | 3/1993 | Sommerkamp |
| 5,201,733 | A | 4/1993 | Etheredge, III |
| 5,261,910 | A | 11/1993 | Warden et al. |
| 5,275,601 | A | 1/1994 | Gogolewski et al. |
| 5,304,180 | A | 4/1994 | Slocum |
| 5,352,228 | A * | 10/1994 | Kummer et al. ............... 606/64 |
| 5,352,229 | A | 10/1994 | Goble et al. |
| 5,356,253 | A | 10/1994 | Whitesell |
| 5,356,410 | A | 10/1994 | Pennig |
| 5,364,399 | A | 11/1994 | Lowery et al. |
| 5,382,248 | A | 1/1995 | Jacobson et al. |
| 5,425,289 | A | 6/1995 | Iwinski |
| 5,429,641 | A | 7/1995 | Gotfried |
| 5,437,667 | A | 8/1995 | Papierski et al. |
| 5,443,466 | A | 8/1995 | Shah |
| 5,458,654 | A | 10/1995 | Tepic |
| 5,470,333 | A | 11/1995 | Ray |
| 5,472,444 | A | 12/1995 | Huebner et al. |
| 5,484,438 | A | 1/1996 | Pennig |
| 5,486,176 | A | 1/1996 | Hildebrand et al. |
| 5,520,690 | A | 5/1996 | Errico et al. |
| 5,527,311 | A | 6/1996 | Procter et al. |
| 5,531,745 | A | 7/1996 | Ray |
| 5,531,746 | A | 7/1996 | Errico et al. |
| 5,536,127 | A | 7/1996 | Pennig |
| 5,549,612 | A | 8/1996 | Yapp et al. |
| 5,558,674 | A | 9/1996 | Heggeness et al. |
| 5,578,035 | A | 11/1996 | Lin |
| 5,586,985 | A | 12/1996 | Putnam et al. |
| 5,591,168 | A | 1/1997 | Judet et al. |
| 5,601,553 | A | 2/1997 | Trebing et al. |
| 5,603,715 | A | 2/1997 | Kessler |
| 5,607,426 | A | 3/1997 | Ralph et al. |
| 5,607,428 | A | 3/1997 | Lin |
| 5,616,144 | A | 4/1997 | Yapp et al. |
| 5,628,740 | A | 5/1997 | Mullane |
| 5,662,655 | A | 9/1997 | Laboureau et al. |
| 5,665,086 | A | 9/1997 | Itoman et al. |
| 5,665,087 | A | 9/1997 | Huebner |
| 5,665,089 | A | 9/1997 | Dall et al. |
| 5,669,915 | A | 9/1997 | Caspar et al. |
| 5,676,667 | A | 10/1997 | Hausman |
| 5,681,311 | A | 10/1997 | Foley et al. |
| 5,709,682 | A | 1/1998 | Medoff |
| 5,709,686 | A | 1/1998 | Talos et al. |
| 5,718,705 | A | 2/1998 | Sammarco |
| 5,728,099 | A | 3/1998 | Tellman et al. |
| 5,733,287 | A | 3/1998 | Tepic et al. |
| 5,749,872 | A | 5/1998 | Kyle et al. |
| 5,766,174 | A * | 6/1998 | Perry .......................... 606/62 |
| 5,772,662 | A | 6/1998 | Chapman et al. |
| 5,776,194 | A | 7/1998 | Mikol et al. |
| 5,785,711 | A | 7/1998 | Errico et al. |
| 5,807,396 | A | 9/1998 | Raveh |
| 5,851,207 | A | 12/1998 | Cesarone |
| 5,853,413 | A | 12/1998 | Carter et al. |
| 5,879,350 | A | 3/1999 | Sherman et al. |
| 5,931,839 | A | 8/1999 | Medoff |
| 5,935,128 | A | 8/1999 | Carter et al. |
| 5,938,664 | A | 8/1999 | Winquist et al. |
| 5,941,878 | A | 8/1999 | Medoff |
| 5,951,557 | A | 9/1999 | Luter |
| 5,954,722 | A | 9/1999 | Bono |
| 5,964,763 | A | 10/1999 | Incavo et al. |
| 5,967,046 | A | 10/1999 | Muller |
| 5,968,046 | A | 10/1999 | Castleman |
| 5,968,047 | A | 10/1999 | Reed |
| 5,989,254 | A | 11/1999 | Katz |
| 6,007,535 | A | 12/1999 | Rayhack et al. |
| 6,010,503 | A | 1/2000 | Richelsoph |
| 6,010,505 | A * | 1/2000 | Asche et al. .................. 606/62 |
| 6,022,350 | A | 2/2000 | Ganem |
| 6,030,389 | A | 2/2000 | Wagner et al. |
| 6,053,917 | A | 4/2000 | Sherman |
| 6,096,040 | A | 8/2000 | Esser |
| 6,123,709 | A | 9/2000 | Jones |
| 6,129,730 | A | 10/2000 | Bono et al. |
| 6,139,550 | A | 10/2000 | Michelson |
| 6,139,552 | A | 10/2000 | Horiuchi |
| 6,146,384 | A | 11/2000 | Lee et al. |
| 6,152,927 | A | 11/2000 | Farris et al. |
| 6,183,475 | B1 | 2/2001 | Lester et al. |
| 6,197,028 | B1 | 3/2001 | Ray et al. |
| 6,206,881 | B1 | 3/2001 | Frigg et al. |
| 6,206,882 | B1 | 3/2001 | Cohen |
| 6,221,073 | B1 | 4/2001 | Weiss et al. |
| D443,060 | S | 5/2001 | Benirschke et al. |
| 6,224,602 | B1 | 5/2001 | Hayes |
| 6,228,085 | B1 | 5/2001 | Theken et al. |
| 6,228,285 | B1 | 5/2001 | Wang et al. |
| 6,231,576 | B1 | 5/2001 | Frigg et al. |
| 6,235,033 | B1 | 5/2001 | Brace et al. |
| 6,235,034 | B1 | 5/2001 | Bray |
| 6,238,395 | B1 | 5/2001 | Bonutti |
| 6,241,736 | B1 | 6/2001 | Sater et al. |
| 6,248,109 | B1 | 6/2001 | Stoffella |
| 6,258,089 | B1 | 7/2001 | Campbell et al. |
| 6,270,499 | B1 * | 8/2001 | Leu et al. ...................... 606/62 |
| 6,283,969 | B1 | 9/2001 | Grusin et al. |
| 6,290,703 | B1 | 9/2001 | Ganem |
| 6,296,642 | B1 | 10/2001 | Morrison et al. |

| Patent Number | Date | Inventor |
|---|---|---|
| 6,322,562 B1 | 11/2001 | Wolter |
| 6,355,041 B1 | 3/2002 | Martin |
| 6,355,043 B1 | 3/2002 | Adam |
| 6,358,250 B1 | 3/2002 | Orbay |
| 6,364,882 B1 | 4/2002 | Orbay |
| 6,379,359 B1 | 4/2002 | Dahners |
| 6,383,186 B1 | 5/2002 | Michelson |
| 6,409,768 B1 | 6/2002 | Tepic et al. |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,468,278 B1 | 10/2002 | Muckter |
| 6,508,819 B1 | 1/2003 | Orbay |
| 6,527,775 B1 | 3/2003 | Warburton |
| 6,540,748 B2 | 4/2003 | Lombardo |
| 6,585,738 B1 | 7/2003 | Mangione et al. |
| 6,595,993 B2 | 7/2003 | Donno et al. |
| 6,599,290 B2 | 7/2003 | Bailey et al. |
| 6,602,255 B1 | 8/2003 | Campbell et al. |
| 6,623,486 B1 | 9/2003 | Weaver et al. |
| 6,626,908 B2 | 9/2003 | Cooper et al. |
| 6,645,212 B2 | 11/2003 | Goldhahn et al. |
| 6,669,700 B1 | 12/2003 | Farris et al. |
| 6,679,883 B2 | 1/2004 | Hawkes et al. |
| 6,692,503 B2 | 2/2004 | Foley |
| 6,706,046 B2 | 3/2004 | Orbay et al. |
| 6,712,820 B2 | 3/2004 | Orbay |
| 6,719,758 B2 | 4/2004 | Beger et al. |
| 6,730,090 B2 | 5/2004 | Orbay et al. |
| 6,730,091 B1 | 5/2004 | Pfefferle et al. |
| 6,755,831 B2 | 6/2004 | Putnam |
| 6,761,719 B2 | 7/2004 | Justis et al. |
| 6,767,351 B2 | 7/2004 | Orbay et al. |
| 6,780,186 B2 | 8/2004 | Errico et al. |
| 6,866,665 B2 | 3/2005 | Orbay |
| 6,926,720 B2 | 8/2005 | Castaneda |
| 6,945,972 B2 | 9/2005 | Frigg et al. |
| 6,955,677 B2 | 10/2005 | Dahners |
| 6,974,461 B1 | 12/2005 | Wolter |
| 7,001,389 B1 | 2/2006 | Navarro et al. |
| 7,048,739 B2 | 5/2006 | Konieczynski et al. |
| 7,063,702 B2 | 6/2006 | Michelson |
| 7,090,676 B2 | 8/2006 | Huebner et al. |
| 7,153,309 B2 | 12/2006 | Huebner et al. |
| 7,179,260 B2 | 2/2007 | Gerlach et al. |
| 7,286,070 B2 | 10/2007 | Zoso et al. |
| 7,326,014 B2 | 2/2008 | Levey et al. |
| 2001/0001119 A1 | 5/2001 | Lombardo |
| 2001/0011172 A1 | 8/2001 | Orbay et al. |
| 2001/0021851 A1 | 9/2001 | Eberlein et al. |
| 2001/0047174 A1 | 11/2001 | Donno et al. |
| 2002/0032446 A1 | 3/2002 | Orbay |
| 2002/0045901 A1 | 4/2002 | Wagner et al. |
| 2002/0049445 A1 | 4/2002 | Hall, IV et al. |
| 2002/0058939 A1 | 5/2002 | Wagner et al. |
| 2002/0058940 A1 | 5/2002 | Frigg et al. |
| 2002/0058941 A1 | 5/2002 | Clark et al. |
| 2002/0111629 A1 | 8/2002 | Phillips |
| 2002/0128654 A1 | 9/2002 | Steger et al. |
| 2002/0143341 A1 | 10/2002 | Biedermann et al. |
| 2002/0147452 A1 | 10/2002 | Medoff et al. |
| 2002/0151899 A1 | 10/2002 | Bailey et al. |
| 2002/0156474 A1 | 10/2002 | Wack et al. |
| 2003/0023240 A1 | 1/2003 | Amrein et al. |
| 2003/0036758 A1 | 2/2003 | Frigg et al. |
| 2003/0045880 A1 | 3/2003 | Michelson |
| 2003/0074068 A1 | 4/2003 | Errico et al. |
| 2003/0078583 A1 | 4/2003 | Biedermann et al. |
| 2003/0083661 A1 | 5/2003 | Orbay et al. |
| 2003/0105461 A1 | 6/2003 | Putnam |
| 2003/0135212 A1* | 7/2003 | Y. Chow ............ 606/64 |
| 2003/0153919 A1 | 8/2003 | Harris |
| 2003/0216735 A1 | 11/2003 | Altarac et al. |
| 2004/0030339 A1 | 2/2004 | Wack et al. |
| 2004/0059334 A1 | 3/2004 | Weaver et al. |
| 2004/0059335 A1 | 3/2004 | Weaver et al. |
| 2004/0068319 A1 | 4/2004 | Cordaro |
| 2004/0073218 A1 | 4/2004 | Dahners |
| 2004/0092935 A1 | 5/2004 | Manderson |
| 2004/0097934 A1 | 5/2004 | Farris et al. |
| 2004/0102778 A1 | 5/2004 | Huebner et al. |
| 2004/0111090 A1 | 6/2004 | Dahners |
| 2004/0193163 A1 | 9/2004 | Orbay |
| 2004/0204712 A1 | 10/2004 | Kolb et al. |
| 2004/0260291 A1 | 12/2004 | Jensen |
| 2004/0261688 A1 | 12/2004 | MacGregor et al. |
| 2004/0267261 A1 | 12/2004 | Derouet |
| 2005/0004574 A1 | 1/2005 | Muckter |
| 2005/0010226 A1 | 1/2005 | Grady, Jr. et al. |
| 2005/0021032 A1 | 1/2005 | Koo |
| 2005/0049594 A1 | 3/2005 | Wack et al. |
| 2005/0080421 A1 | 4/2005 | Weaver et al. |
| 2005/0131413 A1 | 6/2005 | O'Driscoll et al. |
| 2005/0154392 A1 | 7/2005 | Medoff et al. |
| 2005/0165400 A1 | 7/2005 | Fernandez |
| 2005/0187551 A1 | 8/2005 | Orbay et al. |
| 2005/0234455 A1 | 10/2005 | Binder et al. |
| 2005/0261690 A1 | 11/2005 | Binder et al. |
| 2006/0004462 A1 | 1/2006 | Gupta |
| 2006/0009771 A1 | 1/2006 | Orbay |
| 2006/0015101 A1 | 1/2006 | Warburton et al. |
| 2006/0100626 A1 | 5/2006 | Rathbun et al. |
| 2006/0122603 A1 | 6/2006 | Kolb |
| 2006/0149253 A1 | 7/2006 | Doubler et al. |
| 2006/0149255 A1 | 7/2006 | Doubler et al. |
| 2006/0149265 A1 | 7/2006 | James et al. |
| 2006/0200146 A1 | 9/2006 | Doubler et al. |

FOREIGN PATENT DOCUMENTS

| | | |
|---|---|---|
| CH | 675 531 | 10/1990 |
| CN | 1379642 A | 11/2002 |
| DE | 33 01 298 | 2/1984 |
| DE | 40 04 941 | 8/1990 |
| DE | 195 42 116 A | 5/1997 |
| DE | 196 29 011 | 1/1998 |
| DE | 93 21 544 U1 | 9/1999 |
| DE | 43 43 117 C2 | 11/1999 |
| DE | 20200705 | 3/2002 |
| DE | 10115014 A1 | 10/2002 |
| EP | 0451427 A1 | 5/1990 |
| EP | 0486762 B1 | 5/1991 |
| EP | 0451427 A1 | 10/1991 |
| EP | 0689800 | 1/1996 |
| EP | 0988833 | 3/2000 |
| EP | 1086655 A1 | 3/2001 |
| EP | 1250892 A2 | 10/2002 |
| FR | 2233973 A1 | 1/1975 |
| FR | 2405062 A1 | 5/1979 |
| FR | 2855391 | 12/2004 |
| JP | 11047170 A | 2/1999 |
| WO | WO 97/47251 | 12/1997 |
| WO | WO 00/04836 | 2/2000 |
| WO | WO 00/36984 | 6/2000 |
| WO | WO0066011 A1 | 11/2000 |
| WO | WO0112081 A1 | 2/2001 |
| WO | WO 01/19267 A | 3/2001 |
| WO | WO0156452 A2 | 8/2001 |
| WO | WO0215806 A1 | 2/2002 |
| WO | WO 2004/032751 | 4/2004 |
| WO | WO 2004/096067 | 11/2004 |

OTHER PUBLICATIONS

"Numelock II Polyaxial Locking System," Stryker Corporation, brochure.

"SCS.TM./D Distal Radius Plate System: Dorsal", Avanta 1997.
"SCS.TM./V Distal Radius Plate: Volar", Avanta 1998.
"SMARTLock Locking Screw Technology," Stryker Corporation, website description, 2004, www.stryker.Icom.
"Summary of Safety and Effectiveness Information"; Synthes.RTM.; Jul. 29, 1998.
"The Distal Radius Plate Instrument and Implant Set", Technique Guide, Synthes.RTM., Paoli, PA 1995.
"The Titanium Distal Radius Plate", Technique Guide, Synthes. RTM., Paoli, PA, 1995.
"Universal Distal Radius System", Stryker Corporation, website description, 2004, www.stryker.com.
"VAL Plate (Volar Angle Locking) for Distal Radius Fractures", US Implants, brochure.
"Volar Peg Plate Insertion Technique", Trimed, Inc., brochure.
"Volar Radius Plate with Angular Stability", I.T.S. (Implant Technology Systems), 510(k) Summary of Safety and Effectiveness, Feb. 6, 2004.
"Volare Winkelstabile Radiusplatte", I.T.S. (Implant Technology Systems), Spectromed, brochure, 2005, Austria.
Moftakhar, Roham, M.D. and Trost, Gregory R., M.D., "Anterior Cervical Plates: A Historical Perspective", Jan. 2004, pp. 1-5.
Nelson, "Volar Plating with Anatomic Placement and Fixed-Angle Screws", Quick Reference Guide for Contours VPS Volar Plate System by Orthofix, May 2005, www.orthofix.com.
Polyaxial and Monoaxial Spinal Screws, XIA.TM. Spinal System, www.osteonics.com/osteonics/spine/xia2.html, Jun. 25, 2002.
Putnam, D. M.D., "Repair and Rehabilitation of Distal Fractures: The Role of Ssubchondral Fixation" at pp. 144-147.
"Numelock II Polyaxial Locking System," Stryker Corporation, brochure, 2007.
"VAL Plate (Volar Angle Locking) for Distal Radius Fractures", US Implants, brochure, 2007.
"Volar Peg Plate Insertion Technique", Trimed, Inc., brochure, 2007.
"Advances in distal Radius Fracture Management (D)", transcript of American Academy of Orthopaedic Surgeons 2001 Conf.; pp. 134-151, Feb. 28, 2001 including Article by Matthew D. Putnam MD, "Repair and Rehabilitation of Distal Fractures: The Role of Subchondral Fixation" at pp. 144-147.
"Numelock II Polyaxial Locking System," Stryker Corporation, brochure, 2007.
"SCS.TM./D Distal Radius Plate System: Dorsal", Avanta 1997.
"SCS.TM.V Distal Radius Plate: Volar", Avanta 1998.
"SMARTLock Locking Screw Technology," Stryker Corporation, website description, 2004, www.stryker.lcom.
"Summary of Safety and Effectiveness Information"; Synthes.RTM.; Jul. 29, 1998.
"The Distal Radius Plate Instrument and Implant Set", Technique Guide, Synthes.RTM., Paoli, PA 1995.
"The Titanium Distal Radius Plate", Technique Guide, SYNTHES. RTM, Paoli, PA, 1995.
"Universal Distal Radius System", Stryker Corporation, website description, 2004, www.stryker.com.
"VAL PLATE (Volar Angle Locking) for Distal Radius Fractures", US IMPLANTS, brochure, 2007.
"Volar Peg Plate Insertion Technique", TRIMED, Inc., brochure. 2007.
"Volar Radius Plate with Angular Stability", I.T.S. (Implant Technology Systems), 510(k) Summary of Safety and Effectiveness, Feb. 6, 2004.
"Volare Winkelstabile Radiusplatte", I.T.S. (Implant Technology Systems), SPECTROMED, brochure, 2005, Austria.
Moftakhar, Roham, M.D. And Trost, Gregory R., M.D., "Anterior Cervical Plates: A Historical Perspective", Jan. 2004, pp. 1-5.
Nelson, "Volar Plating with Anatomic Placement and Fixed-Angle Screws", Quick Reference Guide for Contours VPS Volar Plate System by ORTHOFIX, May 2005, www.orthofix.com.
Polyaxial and Monoaxial Spinal Screws, XIA.TM. Spinal System, www.osteonics.com/osteonics/spine/xia2.html, Jun. 25, 2002.
Putnam, D. M.D., "Repair and Rehabilitation of Distal Fractures: The Role of Ssubchondral Fixation" at pp. 144-147. 2001.

* cited by examiner

ENDOSTEAL NAIL

BACKGROUND OF THE INVENTION

1. Field of the Invention

This invention relates broadly to surgery. Particularly, this invention relates to orthopedic devices for fracture fixation. More particularly, this invention relates to intramedullary devices for fixation of diaphyseal fractures.

2. State of the Art

Severe long bone fractures are often treated with plating. In plating, a relatively large incision is made at the location of the fracture, musculature and tendons are displaced from the bone to expose the bone surface, and a bone plate is fixedly attached to one or more pieces of the fractured bone in a manner which, ideally, supports and stabilizes the fracture for healing. Due to the relatively invasive nature of the procedure required to implant the plate, plating is generally reserved for fractures which cannot be treated with a less invasive method of immobilization.

Less complicated fractures are often treated with casting or wires. However, such conservative treatment may not provide the stabilization and support necessary for desirable recovery. Yet, the operative procedure of plating is often too invasive for the relative non-severity of the fracture. Moreover, conventional plating can result in tendon irritation and skin necrosis, and may require extensive periosteal stripping in order to apply the plate on the bone surface.

In addition, there is no relatively minimally invasive procedure to treat fractures occurring along a diaphysis of a long bone that also provides the desired reduction and immobilization for such fractures. Furthermore, there is no relatively minimally invasive procedure to treat such fractures that provides the stability generally obtained by more invasive procedures, such as open reduction and internal fixation.

SUMMARY OF THE INVENTION

It is therefore an object of the invention to provide a relatively minimally invasive treatment which provides stabilization and support to long bone fractures.

It is another object of the invention to provide a relatively minimally invasive treatment which provides stabilization and support to diaphyseal fractures.

It is a further object of the invention to provide a implant which is fixedly held within the medullary canal of a long bone.

In accord with these objects, which will be discussed in detail below, an intramedullary nail system is provided. The system includes an elongate nail, bone screws, and a jig system. The nail is designed to be rigidly fixed under compression to the endosteal surface of a bone with unicortical locking machine screws inserted through the bone and a plurality of longitudinally displaced threaded holes in the nail. The screw holes are preferably oriented normal to an endosteal surface of the nail. The screws each include a relatively large head to seat against the outer surface of the bone. As the screws are tightened the nail is forced against the endosteal surface of the bone to effect clamping of the bone between the screw head and the nail. The jig is provided for drilling holes through the bone in alignment with the screw holes in the nail. According to one aspect of the invention, the nail and jig each includes anti-rotation structure by which the nail and jig can be coupled together in a fixed alignment. In a preferred embodiment, such anti-rotation structure on the nail includes a non-circular recess in an endosteal surface of the nail. The recess may be provided at the longitudinal center of the nail, or one or more recesses may be aligned with respective screw holes. The jig has a first portion which extends through the bone and engages within the non-circular recess to lock the jig and the nail in alignment, and a second portion sized to extend over the screw holes of the nail and receive a drill guide to guide a drill to drill holes into bone into alignment with the screw holes therebelow.

In accord with one method of the invention, the nail is introduced into the medullary canal on one side of the fracture, and the nail is then repositioned so that the nail is centered relative to the fracture site and extends substantially equally on each side of the fracture. A hole is drilled through bone and a first screw hole of the nail. The jig is attached at one of the screw holes so that it will not rotate relative to the nail. A drill guide is inserted through respective alignment holes in the jig and holes are drilled through the bone in alignment with screw holes in the nail. The cortical locking screws are then inserted through the drilled holes to clamp the bone between the screw heads and the nail. The jig is removed, and a screw is inserted at the prior location of the jig.

According to another embodiment, the nail includes a central threaded screw hole and non-circular recess at the endosteal surface of the nail in alignment with the central screw hole. A notch is created at the fracture site. The nail is inserted into the medullary canal and the jig is attached to the central screw hole, with the notch defining a space in the bone for the first portion of the jig. The jig is then used to drill holes in the bone in alignment with the screw holes. The screws are then inserted through the bone and nail and tightened to cause the bone to be clamped between the head of the screws and the nail, and the jig is removed from the nail.

The result of the nail and methodology is that a smaller incision can be made, and the operation is relatively minimally invasive with only minor stripping of the periosteal tissue. Furthermore, the nail is easy to insert, being self-guiding into alignment within the medullary canal. The resulting fixation is very stable due to the clamping of the fractured bone between the large screw heads and the nail. Moreover, the large screw heads distribute the stress on the bone over a relatively large surface area on the outer surface of the cortical bone.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
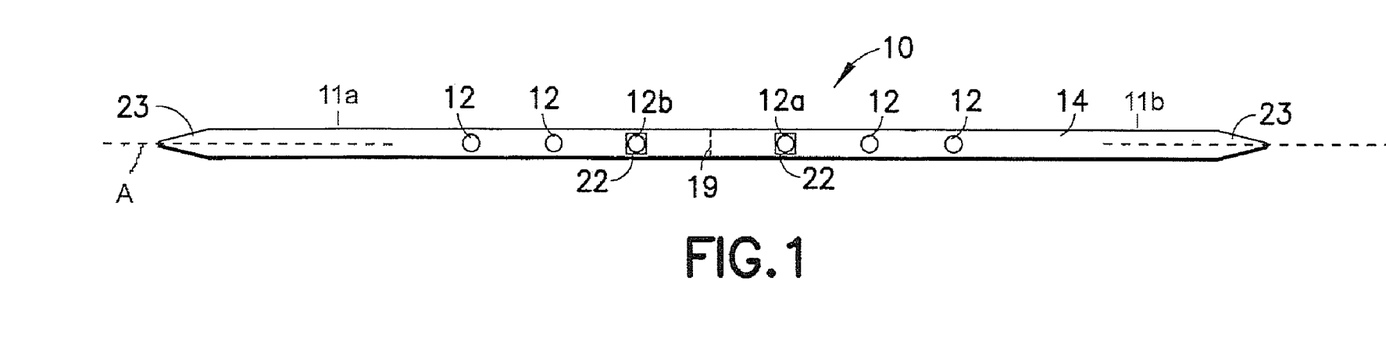
FIG. 1 is a top or endosteal surface view of an intramedullary nail according to the invention.
Figure 2:
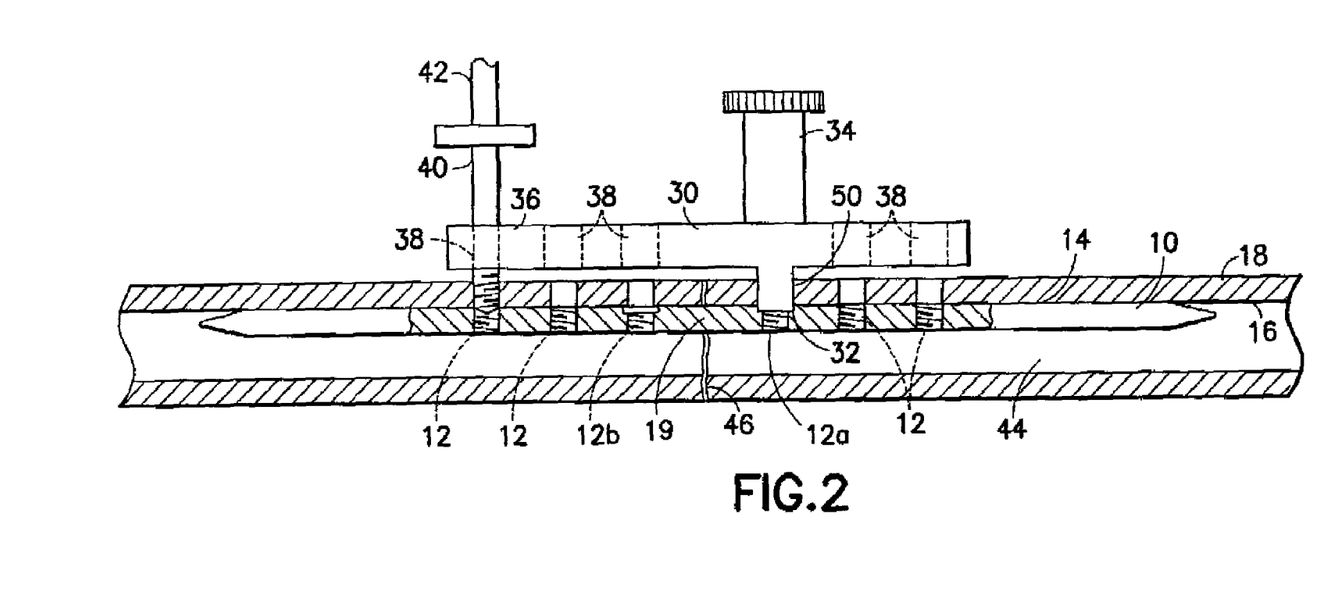
FIG. 2 is a longitudinal section illustrating a method of implanting the nail of FIG. 1 in a fractured bone.
Figure 3:
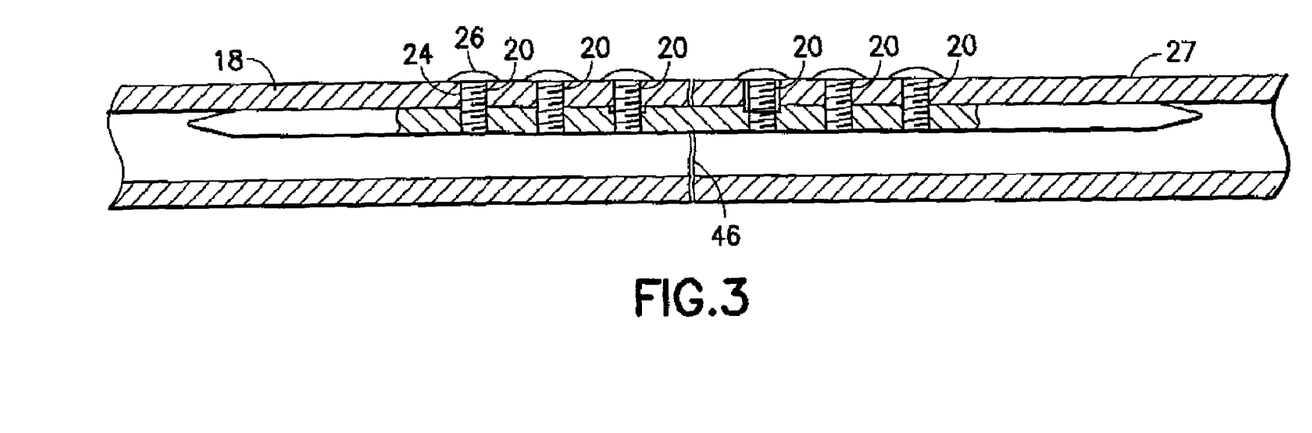
FIG. 3 is a longitudinal section showing the nail of FIG. 1 implanted in a fractured bone.

Turning now to FIGS. 1 through 3, an endosteal nail system according to the invention is shown. The nail 10 of the system includes a plurality of longitudinally displaced screw holes 12 threaded with machine threads. The screw holes are preferably oriented normal to an endosteal surface 14 of the nail. The nail 10 is designed to be rigidly fixed under compression to the endosteal surface 16 of a bone 18 with unicortical locking machine screws 20, discussed below, inserted through the bone 18 and threaded screw holes 12. Over at least one, but preferably two screw holes, a non-circular recess 22 is provided. Such screw holes 12a, 12b provided with the non-circular recess 22 are referred to as 'jig holes', and preferably where two are provided, they are equidistant from the longitudinal center 19 of the nail. The non-circular recess 22 at the jig hole 12a, 12b is square in shape, but may be triangular, hexagonal, star, oval, etc. The ends 23 of the nail 10 are preferably tapered. As seen in FIG. 1, the nail has a longitudinal axis A that defines the dimension of the length of the nail. The center 19 divides the length of the nail into first and second portions 11a, 11b each having their own length equal to one-half the length of the nail. The first and second portions 11a, 11b extend in opposite directions from each other relative to the center 19. As shown, the first and second portions 11a, 11b each have lateral reflective symmetry about the longitudinal axis A, and the first and second portions have longitudinal reflective symmetry with each other about the center 19. The nail 10 preferably has a circular cross-section, but may be have a square, flattened, oval or other cross-sectional shape, or be varied in cross-sectional shape along its length. The nail is preferably titanium alloy or stainless steel in construction.

Referring to FIG. 3, a plurality of locking screws 20 are provided for insertion into the screw holes 12. The screws 20 each include a shaft 24 provided with machine threads to threadably engage the screw holes 12 in the nail and a relatively large head 26 to seat against the outer surface 27 of the bone 18 to effect clamping of the bone between the screw head 26 and the nail 10, as described further below.

Figure 4:
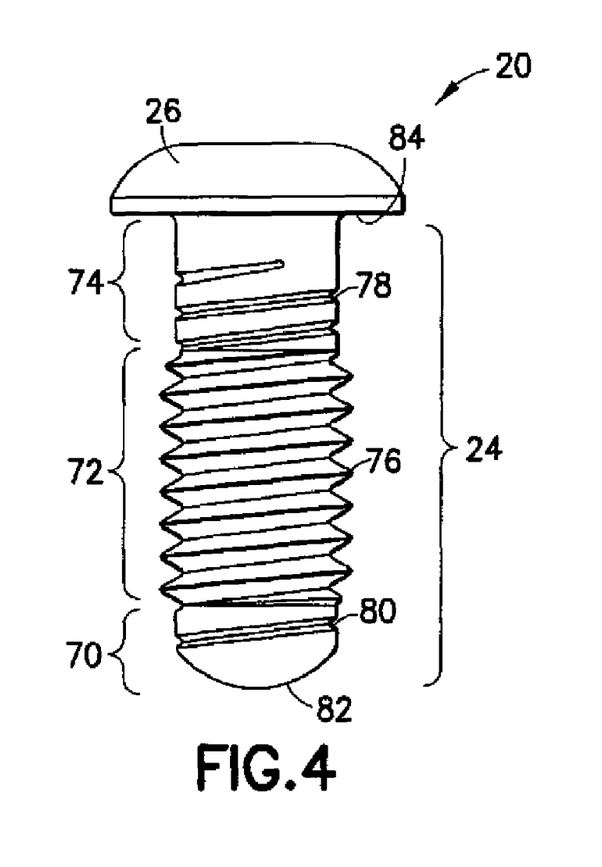
FIG. 4 is a side elevation view of a unicortical machine screw for use in the orthopedic nail system of the invention.
Figure 5:
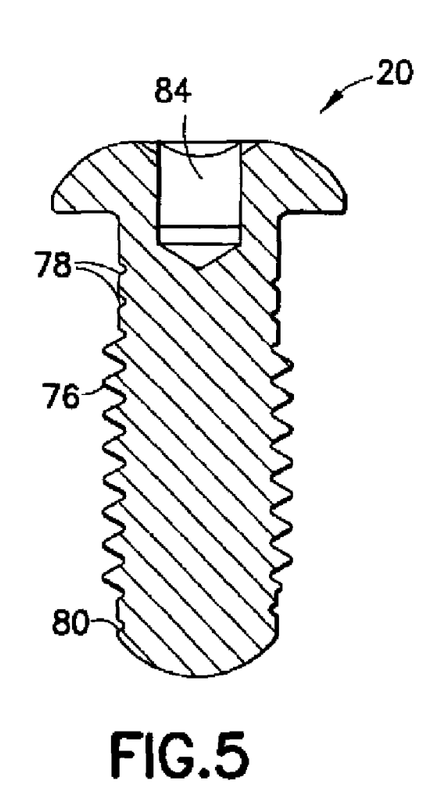
FIG. 5 is a longitudinal section view of the unicortical machine screw of FIG. 4.

More particularly, referring to FIGS. 4 and 5, the screws 20 are preferably unicortical in design. That is, the shaft 24 of each screw 20 is selected in length (for the particular bone being treated) to extend through a near cortex of the bone and to thread into the screw holes 12 of the nail 10, but preferably not to extend beyond the far cortex of the bone. The shaft 24 includes a tip portion 70, a body portion 72, and clearance portion 74. The body portion 72 includes threads 76 adapted to engage in the screw holes 12. In the clearance portion 74, the shaft is relatively smooth, but has a shallow thread channel 78 extending therein which is continuous with and the same pitch as threads 76. The thread channel 78 is sized to accommodate the threads in screw holes 12. The tip portion 70 is preferably also relatively smooth, but slightly smaller in diameter than the clearance portion 74; e.g., a 0.098 inch diameter at the clearance portion 74 versus a 0.095 inch diameter at the tip portion 70. In addition, the tip portion 70 preferably also has a shallow thread channel 80 extending therein which is continuous with and the same pitch as threads 76. The tip portion 70 preferably also has a relatively blunt end 82, as the screw is not intended to tap into bone. In addition, the head 26 of each screw 20 has a substantially flat (planar) undersurface 84 adapted to contact bone and distribute load and stress, and a driver receiving slot 86. In order to distribute load and stress when the bone is under compression, as described hereinafter, the undersurface 84 defines a surface area which is preferably at least 1.5 times larger than an area defined by a cross-section through the shaft 24. Most preferably, the undersurface 84 surface area is approximately $\sqrt{3}$ times larger than an area defined by a cross-section through the shaft 24, but may be even larger to distribute the force over a larger surface area. This preferred ratio provides a suitably large surface area of the head 26 for compression relative to a desirable size of the shaft 24 for stable threaded engagement in the holes 12 in the nail 10.

A jig 30 is provided for drilling holes through the bone 18 in alignment with the screw holes 12 in the nail 10 for insertion of the unicortical screws 20. The jig 30 has a first portion 32 which extends through the bone 18 and includes an end which corresponds in shape and size to engage within said non-circular recess 22. A thumb screw 34 is inserted through the jig 30 into the first portion 32 to lock the jig 30 and nail 10 together at the recess 22 such that the jig and nail cannot rotate relative to each other. The jig 30 includes a second portion 36 which extends over the screw holes 12 of the nail 10 and includes openings 38 that can receive a drill guide 40 to guide a drill 42 to drill holes into the bone 18 into alignment with the screw holes 12 therebelow.

Referring back to FIGS. 2 and 3, in accord with a first method of the invention, the nail 10 is introduced into a medullary canal 44 through a bone fracture 46. For some bones, for example the clavicle, an awl or drill may need to be used to open up the medullary canal prior to nail introduction. The nail 10 is introduced into the medullary canal 44 on one side of the fracture 46, and then repositioned so that the longitudinal center 19 of the nail is at or adjacent the fracture site 46.

A relatively large first hole 50 is drilled freehand through the bone 18, and the drilled hole 50 and a jig hole 12a are aligned. The jig 30 is positioned relative to the jig hole 12a so that the first portion 32 of the jig is engaged within the recess 22 of the jig hole 12a. The jig 30 is then attached with the thumb screw 34 so that it is locked to the nail 10 and will not rotate relative to the nail, thus maintaining openings 38 in alignment over the screw holes 12 of the nail 10 in the medullary canal during the entirety of the procedure. A drill guide 40 is then inserted through respective alignment holes 38 in the jig 30, and holes are drilled with a drill 42 through the bone 18 in alignment with the screw holes 12 in the nail.

The unicortical locking screws 20 are then inserted through the drilled holes to clamp the bone 18 between the screw heads 26 and the nail 10. The jig 30 is removed. A screw 20 is then inserted into jig hole 12a at the prior location of the jig 30. As the screw holes 12 are all oriented normal to the endosteal surface 16 of the nail 10, all the screws 20 are in a preferably parallel linear arrangement which provides maximum clamping force between the nail and screw heads for stability of the fractured bone.

When drilling the holes as described above, it is preferable that holes be drilled in the bone on one side of the fracture, and screws 20 inserted therein into the nail, the fracture then reduced with the bone under compression, and then holes drilled on the other side of the fracture with screws then inserted therein into respective holes in the nail. This order of steps operates to aid in proper healing of the fracture.

Figure 6:
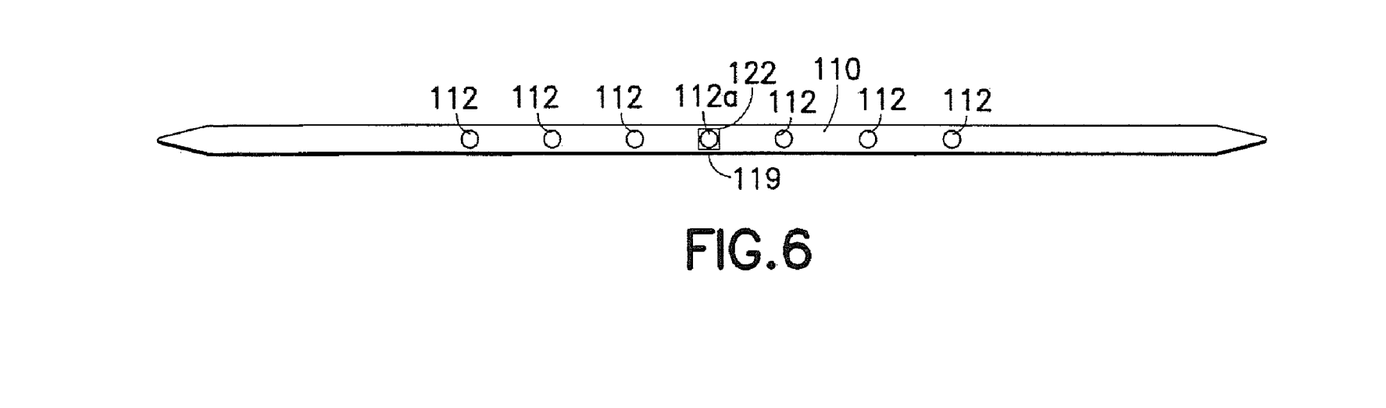
FIG. 6 is a top or endosteal surface view of another embodiment of an intramedullary nail according to the invention.
Figures 7, 8:
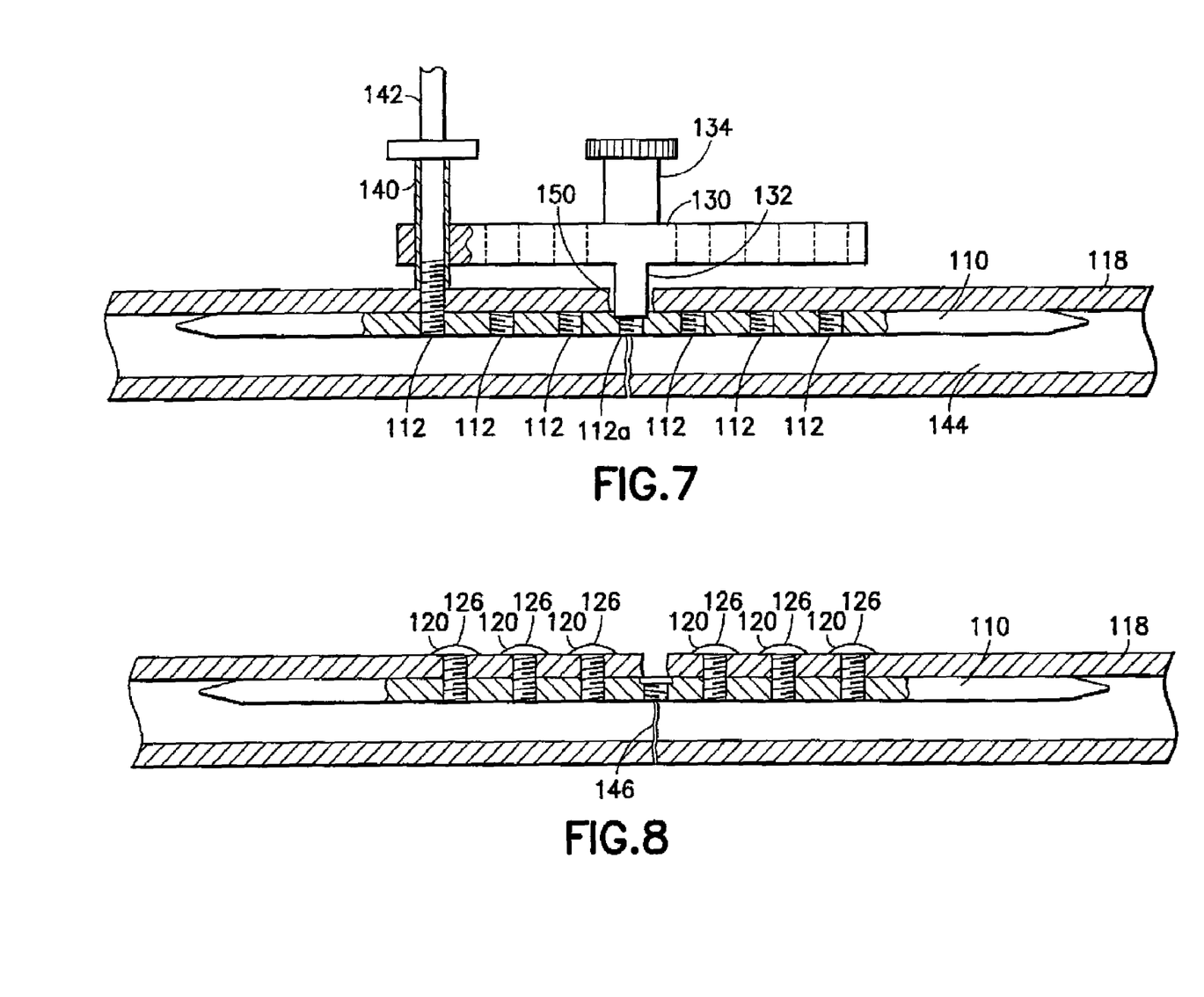
FIG. 7 is a longitudinal section illustrating a method of implanting the nail of FIG. 6 in a fractured bone.
FIG. 8 is a longitudinal section showing the nail of FIG. 6 implanted in a fractured bone.

Referring now to FIGS. 6 through 8, another embodiment of the endosteal nail is shown, substantially similar to the embodiment previously described. In distinction from the prior embodiment, a jig hole 112a and non-circular recess 122 are provided at the longitudinal center 119 of the nail.

Referring to FIGS. 7 and 8, in use, a notch 150 is created at the fracture site 146, e.g., with a rongeur. The nail 110 is inserted into the medullary canal 144 and the jig 130 is attached to the central jig hole 112a with a thumb screw 134, with the notch 150 defining a space in the bone 118 for the first portion 132 of the jig. The jig 134 is then used with a drill guide 140 and drill 142 to drill holes in the bone in alignment with the screw holes 112. The unicortical machine-threaded screws 120 are then inserted through the bone 118 and into the nail 110 and tightened to cause the bone to be clamped between the head 126 of the screws and the nail. The jig 130 is then removed from the nail.

Figure 9:
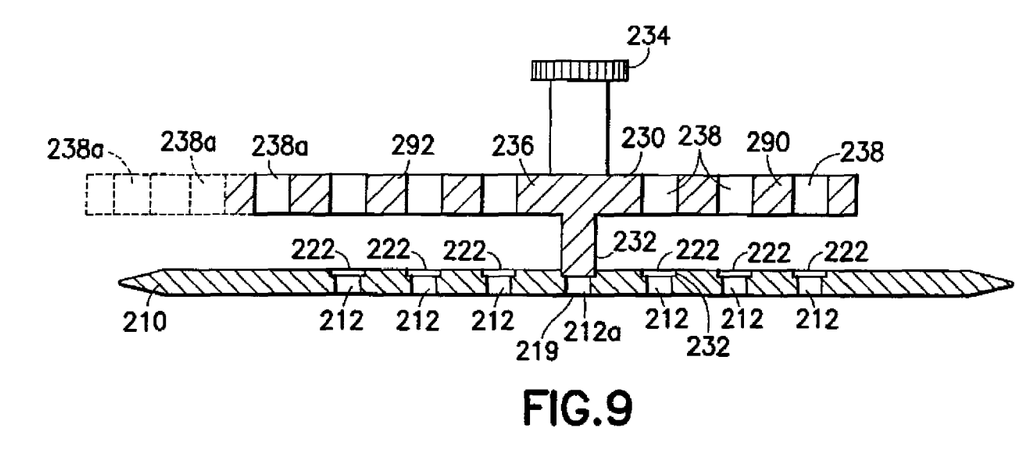
FIG. 9 is a partial section view of a third embodiment of the nail shown with a jig attached at a first location.

Turning now to FIG. 9 a third embodiment of the nail 210 is shown. The nail 210, generally as described above, includes a plurality of screw holes 212 each of which includes a non-circular recess 222 aligned thereover. Also shown is jig 230 which includes first portion 232 which engages within a recess 222, and second portion 236 which extends parallel to the nail 210. Second portion 236 includes a first and second parts 290, 292 which extend over which the screw holes on each side of the longitudinal center 219 of the nail when the jig is attached to a center screw hole 212a. However, the second part 292 is longer than the first part and includes at least one additional opening 238a, for a guide, which extends beyond the screw holes over the respective side when the jig is attached at the center screw hole 212a.

Figure 10:
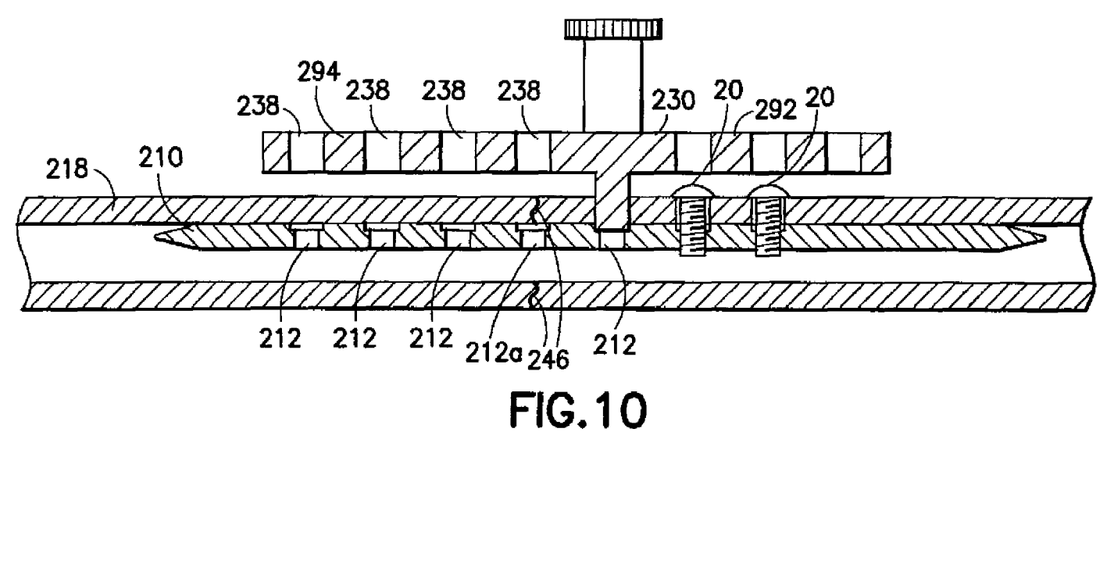
FIG. 10 is a partial section view of the nail of FIG. 10 shown with the jig attached at a second location.

In use, the nail 210 is introduced into the on one side of the fracture, and then repositioned so that the longitudinal center 219 of the nail 210 is at or adjacent the fracture site. The first portion 232 of the jig 230 is placed through the fracture and coupled to preferably the center screw hole 212a of the nail via a thumb screw 234 so that it is locked and will not rotate relative to the nail, thus maintaining openings 238 in alignment over the screw holes 212 of the first part 290 of the jig 230. Then holes are drilled through openings 238 in the first part 292 in alignment with corresponding screw holes 212 on a first side of the fracture. All but one of the drilled holes under the first part 290 is preferably provided with a screw 220. Referring to FIG. 10, the jig 230 is then disengaged from the center screw hole 212a and attached again to the nail 210 through the drilled hole which does not yet include a screw. The fracture 246 is then reduced and compression is applied. While maintaining compression and using openings 238 on the second part 294 of the jig 230, holes are drilled through bone 218 in alignment with the screw holes on the second side of the fracture. Screws are then placed into the drilled holes and maintain the fracture in a reduced and compressed arrangement. The jig 230 is then removed and a final screw is placed in the hole where the jig was previously attached.

As an alternative to using jig 230 and repositioning its location during the procedure, two separate jigs can be used. For example, initially jig 130 may be used at the central screw location 212a. After fracture reduction, jig 30 (or a similar jig of longer length and more openings for drill guides) can be used in a longitudinally offset location.

In all embodiments, it may be possible to attach the jig to the nail prior to insertion of the nail into the bone to facilitate manipulating the bone. In addition, the jig may include alignment structure of a sufficient length such that no separate drill guide is required. Further, it is preferable that the second portion of the jig include at least one side which is adapted to extend over and include openings for all the screw holes on one side of a fracture, and that the other side preferably include openings for at least one screw hole. Such will provide desirable functionality.

The result of the nail, jig system and methodology is that a smaller incision can be made, and the operation is relatively minimally invasive with only minor stripping of the periosteal tissue. Furthermore, the nail is easy to insert, being self-guiding into alignment within the medullary canal. Once implanted, substantially the entire system is intramedullary except for the heads and portions of the shafts of the screws. The resulting fixation is very stable due to the clamping of the fractured bone between the large screw heads and the nail. Moreover, the large screw heads distribute the stress on the bone over a relatively large surface area on the outer surface of the cortical bone.

The nail is suitable for any long bone fracture, particularly the clavicle, radius, and fibula, but may be adapted in size for larger bones such as the femur and tibia. In addition, for curved long bones, e.g., the radius, the nail can be curved.

There have been described and illustrated herein several embodiments of an endosteal nail and a method of stabilizing a fracture with the nail. While particular embodiments of the invention have been described, it is not intended that the invention be limited thereto, as it is intended that the invention be as broad in scope as the art will allow and that the specification be read likewise. Thus, while particular materials and shapes for the nail have been disclosed, it will be appreciated that other suitable materials and shapes may be used as well. In addition, in each embodiment, jig holes may be provided both at the center and offset from the center of the nail, and may be provided over each screw hole. It will therefore be appreciated by those skilled in the art that yet other modifications could be made to the provided invention without deviating from its spirit and scope as claimed.

What is claimed is:

1. An intramedullary nail system for use with a jig, comprising:
    an elongate nail including at least four threaded parallel screw holes in linear arrangement, said screw holes oriented normal to an endosteal surface of said nail, and a non-circular recess located at the upper portion of one of said threaded parallel screw holes of said linear arrangement, said recess for mating with a portion of the jig to lock the jig in a rotational orientation relative to said nail, said nail having a longitudinal axis defining the length of said nail and a center along said longitudinal axis which divides said nail into first and second portions each having a length equal to one-half the length of said nail, said first and second portions extending in opposite directions from each other relative to said center, wherein said first portion has lateral reflection symmetry about said longitudinal axis, said second portion has lateral reflection symmetry about said longitudinal axis, and said first and second portions have longitudinal reflection symmetry with each other about said center.

2. A nail system according to claim 1, wherein:
    said non-circular recess is square or rectangular.

3. A nail system according to claim 1, wherein:
    an equal number of said threaded parallel screw holes are provided along each of said first and second portions.

4. A nail system according to claim 1, wherein:
    said nail includes first and second ends which are tapered.

5. A nail system according to claim 1, further comprising:
    a plurality of unicortical machine screws each having a head and a shaft configured to threadably engage in one of said threaded parallel screw holes,
        wherein when said screws are insertable through bone and into said screw holes the bone is clamped between said head of said screws and said endosteal surface of said nail.

6. A nail system according to claim 5, wherein:
said head of each of said screws have an undersurface for contacting bone which define a surface area, and said shaft of each of said screws having a cross-sectional area defined by a cross-section through said shaft, wherein the ratio of said surface area of said undersurface said cross-sectional area is at least 1.5.

7. An orthopedic nail system according to claim 6, wherein:
the ratio of said surface area to said cross-sectional area is approximately $\sqrt{3}$.

8. An orthopedic nail system according to claim 6, wherein:
the ratio of said surface area to said cross-sectional area is at least approximately $\sqrt{3}$.

9. An orthopedic nail system according to claim 6, wherein:
said undersurface is substantially flat.

10. A nail system according to claim 1, wherein:
said endosteal surface includes at most one non-circular recess.

11. A nail system according to claim 1, wherein:
said endosteal surface includes at most two non-circular recesses.

12. A nail system according to claim 1, wherein:
said recess has a polygonal shape.

13. A nail system according to claim 1, wherein:
a plurality of said threaded screw holes of said linear arrangement each include a recess at an upper portion thereof.

14. An orthopedic nail system for use with a jig, comprising:
a) an elongate nail including at least four threaded screw holes in linear arrangement oriented normal to an endosteal surface of said nail, and a non-circular recess located at the upper portion of one of said threaded parallel screw holes of said linear arrangement, said recess for mating with a portion of the jig to lock the jig in a rotational orientation relative to said nail,
said nail having a longitudinal axis defining the length of said nail and a center along said longitudinal axis which divides said nail into first and second portions each having a length equal to one-half the length of said nail, said first and second portions extending in opposite directions from each other relative to said center, wherein said first portion has lateral reflection symmetry about said longitudinal axis, said second portion has lateral reflection symmetry about said longitudinal axis, and said first and second portions have longitudinal reflection symmetry with each other about said center; and
b) a plurality of unicortical machine screws each having a head and a shaft configured to threadably engage in one of said screw holes, said head having an undersurface for contacting bone, said undersurface defining a surface area, and cross-sectional area being defined by a cross-section through said shaft, wherein the ratio of said surface area of said undersurface of said head to said cross-sectional area through said shaft is at least 1.5.

15. An orthopedic nail system according to claim 14, wherein:
the ratio of said surface area of said undersurface of said head to said cross-sectional area through said shaft is approximately $\sqrt{3}$.

16. An orthopedic nail system according to claim 15, wherein:
the ratio of said surface area of said undersurface of said head to said cross-sectional area through said shaft is at least approximately $\sqrt{3}$.

17. An orthopedic nail system according to claim 15, wherein:
said undersurface is substantially flat.

18. An orthopedic nail system according to claim 15, wherein:
said recess has a polygonal shape.

19. An orthopedic nail system according to claim 15, wherein:
a plurality of said threaded screw holes of said linear arrangement each include a recess at an upper portion thereof.

* * * * *